United States Patent [19]
Kellett et al.

[11] Patent Number: 4,856,541
[45] Date of Patent: Aug. 15, 1989

[54] BRUSH INCORPORATING A HYDROPHILIC FOAM PAD FOR HAIR CLEANING AND CONDITIONING

[75] Inventors: George W. Kellett, Cranford; Betty J. Murphy, Upper Montclair, both of N.J.

[73] Assignee: Creative Products Resource Associates, Ltd., Elizabeth, N.J.

[21] Appl. No.: 82,437

[22] Filed: Aug. 6, 1987

[51] Int. Cl.⁴ .................... A45D 19/00; A45D 24/00; A45D 24/16
[52] U.S. Cl. .................. 132/110; 132/108; 132/111; 521/52; 252/91; 252/DIG. 3; 252/DIG. 13; 424/70; 15/104.93; 15/104.94; 401/283
[58] Field of Search ............. 132/7, 85, 88.7, DIG. 3, 132/108, 109, 110, 111; 521/52; 134/40; 252/106, DIG. 3, DIG. 5, DIG. 7, DIG. 13, 91; 106/4, 8, 9; 424/70; 15/104.93, 104.94; 401/283

[56] References Cited

U.S. PATENT DOCUMENTS

| | | | |
|---|---|---|---|
| 3,088,158 | 5/1963 | Boyle et al. | 15/506 |
| 3,447,181 | 6/1969 | Coker et al. | 252/91 |
| 3,833,008 | 9/1974 | Blackett, Jr. et al. | 132/85 |
| 4,066,394 | 12/1974 | Leonard | 8/137 |
| 4,127,515 | 11/1978 | MacRae et al. | 521/112 |
| 4,137,200 | 1/1979 | Wood et al. | 521/159 |
| 4,157,388 | 6/1979 | Christiansen | 252/DIG. 3 |
| 4,206,195 | 6/1980 | Bolich, Jr. et al. | 424/70 |
| 4,271,272 | 6/1981 | Strickman et al. | 521/110 |
| 4,343,910 | 8/1982 | Busch, Jr. et al. | 521/82 |
| 4,548,954 | 10/1985 | Smith et al. | 521/52 |
| 4,563,483 | 1/1986 | Smith et al. | 521/111 |
| 4,565,644 | 1/1986 | Smith et al. | 252/94 |
| 4,569,861 | 2/1986 | Smith et al. | 427/244 |
| 4,581,385 | 4/1986 | Smith et al. | 521/111 |
| 4,594,362 | 6/1986 | Smith et al. | 521/52 |
| 4,740,367 | 4/1988 | Force et al. | 424/70 |
| 4,806,572 | 2/1989 | Kellett | 252/91 |

*Primary Examiner*—Richard J. Apley
*Assistant Examiner*—Paul Prebilic
*Attorney, Agent, or Firm*—Merchant, Gould, Smith, Edell, Welter & Schmidt

[57] ABSTRACT

A hair cleaning and conditioning pad is provided which comprises a shaped body of a resilient, open-celled, hydrophilic polyurethane foam matrix integrally incorporating an aqueous phase incorporating about 70-90% water, about 1-20% of a water-immiscible organic solvent, about 0.05-1.5% of a hair conditioning agent and a mixture of surfactants comprising a nonionic surfactant, a cationic surfactant and, optionally, an amphoteric surfactant. The pad is preferably affixed to the tines of a styling brush to yield a composite brush which is effective to clean and condition dry hair.

26 Claims, 2 Drawing Sheets

BRUSH INCORPORATING A HYDROPHILIC FOAM PAD FOR HAIR CLEANING AND CONDITIONING

BACKGROUND OF THE INVENTION

Liquid shampoos are commonly employed to clean the hair of humans and animals which have been soiled with dirt, grease, sweat, odors and environmental soils. Typically, the hair is thoroughly wetted, an amount of the shampoo is manually rubbed into the hair, and the treated hair is rinsed clean. Liquid conditioning agents to enhance the manageability and appearance of the hair can optionally be applied to the hair prior to the final water rinse and drying steps.

Typically, shampoos contain aqueous solutions or dispersions of detergents and alcoholic solvents to solubilize oils and other greasy substances, along with emollient oils and waxes. Shampoos can also include agents to treat dermatological conditions such as dandruff, or to control insect pests on animals. Conditioning agents include materials which are substantive to hair, e.g., are absorbed onto the hair. Such agents include various modified proteins and film-forming synthetic polymers.

Although liquid shampoos and substantive agents can be effective to clean and condition hair, they must be applied and removed in conjunction with the application of large amounts of water to the hair of the user. This process can be inconvenient and time-consuming, especially due to the drying and styling steps necessary after the hair has been washed. If the hair is not really dirty, but only needs freshening, there is no convenient and effective conventional way of revitalizing and refreshing, without shampooing.

Therefore, a need exists for a method which is effective to rapidly clean and condition hair without unduly wetting the hair or necessitating a drying step.

BRIEF DESCRIPTION OF THE INVENTION

The present invention is directed to a cleaner and conditioner for use on dry hair which comprises a shaped body of a resilient, open-celled hydrophilic polyurethane foam. The polyurethane foam is formed by reaction of selected prepolymer resins with an aqueous phase, which becomes incorporated into and bonded to the cell walls of the cured foam matrix without substantially occluding the cellular voids. This "interior aqueous phase" is formulated to contain surfactants and solvents in amounts which are effective to disperse or dissolve oily soil when the foam body is contacted with dry hair. The interior aqueous phase can also contain polymeric conditioning agents. Optional ingredients which can be dispersed in the aqueous reactant phase and incorporated into the foam body include particulate absorbents, fragrances, antimicrobial agents, insecticides and the like.

Preferred foam pads prepared in accord with the invention are resilient and possess an open-celled matrix which is highly reticulated in the sense that the area occupied by cell walls is relatively small compared to the total cellular volume. These characteristics permit the pad to effectively contact the individual hairs, and to release an amount of the interior aqueous phase effective to solubilize, disperse and pick up oily soils while depositing conditioners on the hair.

It is also advantageous to incorporate a minor amount of an inorganic salt such as sodium chloride (NaCl) into the aqueous phase. Surprisingly, it was found that about 0.05–2.5% of NaCl substantially increased the amount of the aqueous phase which was released from the foam matrix during use, without unduly irritating the skin of the user.

As used herein, the term "pad" is intended to encompass any shaped foam body which is useful for manual application to the hair, including sticks, blocks, sheets and discs of hydrophilic foam. The term "resilient" is intended to indicate that the pads maintain their integrity during use, e.g., are not friable. Although dry hair can be cleaned and conditioned by rubbing it manually with the pad, it is highly preferable that an appropriately-sized pad be impaled on the tines of a styling brush. Thus secured, the pad can effectively contact the hair when the hair is brushed by the user. Thus, the styling brush and the pad secured thereon form a novel composite hair cleaning and conditioning brush, which is also an embodiment of the present invention. Preferred pads for use in conjunction with commercially available styling brushes are shaped into rectangular or cylindrical blocks, and comprise a substantial number of large cells, e.g., cells which are about 1.0–5.0 mm in diameter. This open, highly-reticulated structure permits the foam pad to be easily affixed to the styling brush by the user, since the relatively rigid tines of the brush can readily pass entirely through the foam pad.

The finished pads will incorporate a high weight percentage of aqueous reactant phase to polymeric foam matrix, e.g., a ratio of aqueous reactant phase: prepolymer resin of up to about 3:1 can be employed. However, due to the high affinity of the interior aqueous phase for the matrix fibrils, the finished pads are only slightly slick to the touch and do not significantly moisten the hair during use. The hair is left clean, fragrant, and conditioned in the sense that hair body, sheen and volume are improved. Furthermore, the cleaners can incorporate and release effective amounts of therapeutic dermatological agents and insecticidal agents.

The use of large amounts of an aqueous dispersion of active ingredients to foam the prepolymer resin also completely eliminates the need to post-add water or other cleaning liquids to the preformed foams. In contrast to foam pads such as the wax-containing pad disclosed by McRae et al. (U.S. Pat. No. 4,127,515) which must be moistened prior to use, the addition of water to the present pads would be deleterious in that the added water would dilute the interior aqueous phase. Furthermore, the excess water would destroy the ability of the present pad to release the interior aqueous phase in a controlled fashion, leading to dripping and running during use.

All percentages are weight percentages unless otherwise indicated. Percentages of commercially available materials, such as emollient oils, have been adjusted downward, if necessary, so that they represent only the active component or components, and do not include water or other solvents. Common chemical names of ingredients are given in accord with the *CTFA Cosmetic Ingredient Dictionary*, the Cosmetic, Toiletry and Fragrance Assoc., Inc., Pub., Washington, D.C. (3d ed. 1982, and 3d 3d., supp. 1985).

BRIEF DESCRIPTION OF THE DRAWINGS

The drawings constitute a part of the specification and include exemplary embodiments of the present invention, while illustrating various objects and features thereof. In some instances relative material thicknesses, and sizes, may be shown exaggerated to facilitate an understanding of the invention.

DETAILED DESCRIPTION OF THE INVENTION

Figure 1:
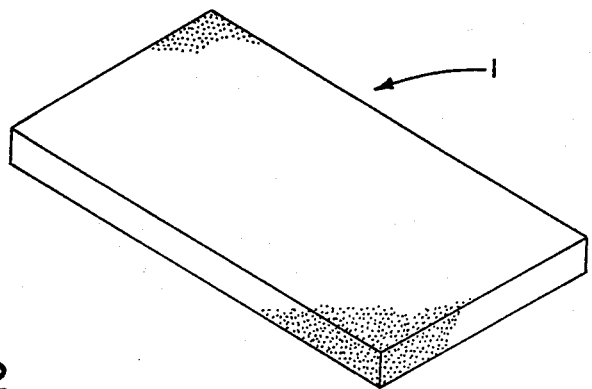
FIG. 1 is a perspective view of a foam pad according to the present invention.

The hair cleaning and conditioning pads of the present invention are prepared by a process comprising forming an aqueous dispersion comprising a solvent, a nonionic surfactant, an anionic surfactant, and a polymeric hair conditioning agent. Optional ingredients which can be incorporated in the aqueous dispersion include an inorganic salt, an amphoteric surfactant, a particulate absorbent and a silane coupling agent, biocides, fragrance and preservative. The fully formed aqueous dispersion is then combined with a water-foamable prepolymer resin and the reaction mixture allowed to foam and cure to yield a self-crosslinked, open-celled, resilient polyurethane foam body. The foam may be cured to the desired final shape in an appropriately formed mold, or may be cut into the end-use configuration from a larger body.

Prepolymer Resins

A commercially available class of water foamable prepolymer resins which yield cross-linked, hydrophilic polyurethane foams upon the addition of stoichiometric excesses of water are those belonging to the Hypol® series (W. R. Grace & Co., Lexington, Mass.; FHP 5000, 4000, 3000, 2000, 2000 HD, 2002) which are generally described in U.S. Pat. No. 4,137,200 and in the W. R. Grace & Co. technical bulletins, *Hypol®* and *Hypol Plus® Foamable Hydrophilic Prepolymers*, the disclosures of which are incorporated by reference herein. These liquid resins are prepared by capping mixtures of low molecular weight polyols having 308 hydroxyl groups and polyoxyethylene diols with toluene diisocyanate. The capped alcohol mixtures have an average number of free isocyanate groups per molecule which is equal to two or more, e.g., 2 to 8.

These resins possess molecular weights within the range of about 1300–1400 and have about 1.5–2.6 mEq./g. of free isocyanate groups. Upon being contacted with a molar excess of water, the isocyanate groups hydrolyze to release carbon dioxide gas, thus foaming the resin without the need for added catalysts or blowing agents. The free amino groups formed by the hydrolysis reaction react with unhydrolyzed isocyanate groups to form ureido groups which cross-link and stabilize the foam, while entrapping a part of the excess water in the cell walls, where it acts to impart hydrophilic properties to the foam. The compatibility of the foam matrix with large molar excesses of water is a necessary requirement of resins useful in the practice of the present invention, since large amounts of water are needed to uniformly introduce large amounts of hydrophobic solvents and absorbents into the matrix.

Other poly-$C_2$-$C_3$-alkylenoxy glycols capped with aromatic isocyanates may be prepared which possess a suitable balance between their extent of cross-linking prior to foaming and their ability to cross-link or to further cross-link during foaming (due to the presence of more than two reactive isocyanate groups per resin molecule), so as to be useful in the practice of the present invention over the entire range of solvent, conditioner and surfactant content. These prepolymer resins are prepared by polymerizing ethylene oxide to yield polyalkylenoxy polyols having a molecular weight of about 900–1100. These polyols are reacted with a stoichiometric excess of a polyisocyanate. Suitable isocyanates include toluene diisocyanate, triphenylmethane-4,4'4''-triisocyanate, benzene-1,3,5-triisocyanate, hexamethylene diisocyanate, xylene diisocyanate, chlorophenylene diisocyanate and mixtures thereof. The useful resins recovered have a somewhat lower number of mEl of free isocyanate groups (NCO) per gram of resin than do the Hypol® resins, e.g., 1.3–1.5 mEq./gram and can exhibit substantially higher ensile strengths when foamed and cured at ambient temperatures.

Commercially available self-crosslinking resins include Trepol® A-62 and TRE STD® prepolymer resin (Twin Rivers Engineering Co., East Booth Bay, Me.), which form acceptable foams upon reaction with at least a stoichiometric excess of water without employing a low molecular weight polyol component to raise the average number of free isocyanate groups per glycol ether molecule to above two. TRE STD® resin has an average free isocyanate content of about 1.4 mEq./gram, comprises a polyol component having an average molecular weight of about 1000, exhibit a viscosity at 32° C. of 4700 cps and solidifies at 15.5° C.

In the practice of the present invention, useful foams may be formed employing a weight ratio of water to prepolymer resin of about 3.0–1.0:1, preferably about 2.5–1.5:1, most preferably about 2.3–1.9:1.0. These ranges represent mole ratios of water to free isocyanate groups of about 20–150:1, preferably about 30–135:1.

These amounts of water react with the free isocyanate groups to release carbon dioxide which blows the prepolymer into a cross-linked, open-celled foam which is rendered hydrophilic by entrapment of excess water in the cell walls of the foam matrix. When the prepolymer-slurry mixture is allowed to set in molds, a flexible, resilient foam body of the desired shape is formed.

Solvent

About 0.5–17.5% by weight of the aqueous phase may also consist of a nontoxic organic solvent such as petroleum ether, napthol spirits, mineral spirits, paraffin oil, low viscosity silicone fluids (dimethyl polysiloxanes), m-pyrol, tetrahydrofurfuryl alcohol (THFA), or a similar aromatic or aliphatic solvent or solvent mixture. The solvent functions to aid in the solubilization and removal of greasy and oily soils, and contributes to the non-uniform cell size which is achieved. Preferably, the solvent will be selected from those which are water-insoluble, e.g., the synthetically produced isoparaffinic solvents which are commercially available as the Isopar® series from Exxon Corp. (Houston, Tex.). However, minor amounts of water-soluble solvents such as the lower alkanols, THFA and the like, may also be included since such solvents substantially assist the solubilization of dispersal of the water-insoluble components of the aqueous reactant phase. Although the water-insoluble solvents preferred for use in the present invention destabilize the aqueous reactant phase, the homogeneity of the aqueous reactant phase can be satisfactorily maintained by stirring, until it is mixed with the prepolymer resin.

However, once the foaming reaction has been completed, it is believed that the water-insoluble solvent acts to break the emulsion, and thus to facilitate the release of other cleaning and conditioning components from the foam matrix while the water is substantially retained. It is also preferred that the organic solvent be relatively volatile, so that it is not significantly retained on the hair.

Polymeric Conditioning Agent

The aqueous reactant phase will also be formulated to comprise an effective amount of a conditioning agent. Useful conditioning agents include film-forming resins which are water-soluble or water-dispersable, and which are substantive to the hair, in that they are absorbed by the hair. The bound conditioners act to modify the properties of the hair, i.e., to improve its feel, manageability, compatibility, body, sheen and to repair split ends.

One useful conditioner is hydrolyzed animal protein. These collagenous materials are commercially available under a variety of designations, e.g., as Nutrilan ® (Henkel Corp., Ambler, Pa.; m.w. 500–2000) or as Peptein ® 2000 (Hormel & Co., Austin, Minn.; 55% min. solids, pH 5.8–6.3). Collagen derivatives in which collagen has been chemically modified to attach cationic groups thereto are also useful as conditioners in the present invention. They include lauryldimonium hydroxypropylamino hydrolyzed animal protein (Lamequat ® L, Henkel Corp., m.w. 600–700); and protein abietic acid condensate, triethanol amine salt (CTFA: TEA-Abietoyl-Hydrolyzed Animal Protein (Lamepon ® PA-TR, Henkel Corp.)).

Other collagen derivative which can be employed as conditioners include potassium undecylenoyl hydrolyzed animal protein, which can also function as an antidandruff agent (Lamepon ® UD, Henkel Corp.); potassium coco-hydrolyzed animal protein (Lamepon ® S, Henkel Corp.); and triethanolamin-coco-hydrolyzed animal protein (Lamepon ® S-TR; Henkel Corp., m.w. 790–890, 11–13% protein; and Lamepon ® ST 40; Henkel Corp., m.w. 790–890, 14–16% protein).

Other useful cationic polymeric conditioning agents include the cationic cellulosic polymers available as Celquat ® H-100 and H-200 (National Starch & Chem. Corp., Bridgewater, N.J.).

Other totally synthetic organic polymeric conditioners can be employed, including the vinylpyrrolidone/dimethylaminoethylmethacrylate copolymer available from GAF Corp. (Wayne, N.J.) as Gafquat ® 755N polymer (high molecular weight) or the vinylcaprolactam/vinyl acetate copolymers PVP/VA E-735 (mole ratio 70:30); PVP/VA E-635 (mole ratio 60/40) and PVP/VA E-535 (mole ratio 50/50); and the polyvinylpyrrolidones available as PVP K-30 (m.w. 40,000) and PVP K-60 (m.w. 160,000). Amion-functionalized polydimethyl siloxanes can also be employed as cationic polymeric conditioners, e.g., Dow Corning ® 929 Cationic Emulsion (35% silicone content, pH 7.6).

Surfactant

One or more foam-reticulating surfactants will also be incorporated into the aqueous phase. These surfactants function to remove the window membranes of the foam cells, thus producing the desired reticulated, or highly open, structure. The surfactant also enhances the cleaning power of the foam by dispersing oily or greasy soils when the foam is brought into contact with the hair. Foam reticulating surfactants are preferably selected from a mixture of nonionic surfactants and anionic surfactants, which optionally include amphoteric surfactants.

Useful nonionic surfactants include the polyoxyalkylene block copolymers formed by condensing ethylene oxide with a hydrophobic polyoxyalkylene base formed by the condensation of propylene oxide with propylene glycol. The hydrophobic portion of these compounds has a molecular weight sufficiently high so as to render it water-insoluble. The addition of polyoxyethylene moieties to this hydrophobic portion increases the water solubility of the molecule as a whole, and the liquid character of the product is retained up to the point where the polyoxyethylene content is about 50% of the total weight of the condensation product.

Examples of compounds of this type include certain of the commercially available Pluronic ® surfactants (CTFA designation: Poloxamer series, BASF Wyandotte Corp., Wyandotte, Mich.). Preferably, a mixture of this class of nonionic surfactants will be used, e.g., a mixture of those in which the polyoxypropylene ether has a molecular weight of about 1750–2250 and (a) the polyoxyethylene content is about 10–30% of the molecule by weight, i.e., Pluronic ® L-62, L-72 and L-92; with (b) one in which the polyoxyethylene content is about 40–60% of the molecule by weight, e.g., Pluronic ® P-75.

A mixture of a "low polyoxyethylene" polymer with a "high polyoxyethylene" polymer apparently contributes to increasing the population of larger cells in the foam. For example, a preferred weight ratio of L-62:P-75 is about 10–5:1.

Other useful nonionic surfactants for use in the present invention are the alkanol amides of ($C_{10}$–$C_{22}$) fatty acids, preferably, the diethanolamide, monoisopropanolamide or monoethanolamides of ($C_{12}$–$C_{18}$) fatty acids. These compounds are commercially available as the Standamid ® series (Henkel Corp.) e.g., lauramide DEA, cocamide DEA and cocamide MEA. Other useful compounds of this type include stearamide MEA, stearamide MIPA, stearamide DEA, myristamide DEA, myristamide MEA, myristamide MIPA and the like.

Another preferred class of nonionic surfactants is the fatty acid esters of $C_2$–$C_5$-polyols, e.g., the ($C_8$–$C_{22}$) fatty acid monoesters of glycerol, propylene glycol, ethylene glycol, sorbitol and the like. For example, glyceryl monostearate is commercially available as Cerasynt ® 945 from Van Dyk & Co., Belleville, N.J.

Other useful nonionic surfactants include the condensation products of $C_8$–$C_{22}$ alkyl alcohols with 2–50 moles of ethylene oxide per mole of alcohol. Examples of compounds of this type include the condensation products of $C_{11}$–$C_{15}$ fatty alcohols with 3–50 moles of ethylene oxide per mole of alcohol which are commercially available from Shell Chemical Co., Houston, Tex., as, i.e., Neodol ® 23-6.5 ($C_{12}$–$C_{13}$ fatty alcohol condensed with about 7 moles of ethylene oxide), the Poly Tergent ® SLF series from Olin Chemicals or the Tergitol ® series from Union Carbide, e.g., Tergitol ® 15-S-15, which is forced by condensing about 15 moles of ethylene oxide with a $C_{11}$–$C_{15}$ secondary alkanol; and Tergitol® TMN-6, which is the condensation product of about 6 moles of ethylene oxide with isolauryl alcohol (CTFA name: isolaureth-6). Another commercially available nonionic surfactant of this class is the condensation product of lauryl alcohol with about 11–40 moles of ethylene oxide, e.g., Lipocol® L-23 (OEt$_{23}$)(Lipo Chemicals, Inc., Paterson, N.J.).

Other nonionic surfactants which may be employed include the ethylene oxide esters of $C_6$–$C_{12}$ alkyl phenols such as (nonylphenoxy)polyoxyethylene ether. Particularly useful are the esters prepared by condensing about 8–12 moles of ethylene oxide with nonylphenol, i.e., the Igepal® CO series (GAF Corp., New York, N.Y.).

Other useful nonionics include the ethylene oxide esters of alkyl mercaptans such as dodecyl mercaptan polyoxyethylene thioether, the ethylene oxide esters of fatty acids such as the lauric ester of polyethylene glycol and the lauric ester of methoxypolyethylene glycol, the ethylene oxide ethers of fatty acid amides, the condensation products of ethylene oxide with partially fatty acid esters of sorbitol such as the lauric ester of sorbitan polyethylene glycol ether, and other similar materials, wherein the mole ratio of ethylene oxide to the acid, phenol, amid or alcohol is about 5-50:1.

Useful anionic surfactants include the ammonium or alkali metal salts of sulfated ethylenoxy fatty alcohols (the sodium, ammonium sulfates of the condensation products of about 1–4 moles of ethylene oxide with a $C_{12}$–$C_{15}$ n-alkanol, i.e., the Neodol® ethoxysulfates, such as Neodol® 25-3S, Shell Chemical Co.); the alkali metal, ammonium or alkanol amine salts of sulfated ($C_8$–$C_{22}$) fatty alcohols (e.g., the Standapol® series, Henkel Corp., including DEA-lauryl sulfate, MEA-lauryl sulfate, sodium lauryl sulfate, TEA-lauryl sulfate, and the like); and anionic detergent salts having alkyl substituents of 8 to 22 carbon atoms such as the water-soluble higher fatty acid alkali metal, ammonium or amine soaps, e.g., sodium myristate and sodium palmitate.

Another useful class of anionic surfactants encompasses the water-soluble sulfated and sulfonated anionic alkali metal and alkaline earth metal detergent salts containing a hydrophobic aromatic moiety (typically containing from about 8 to 22 carbon atoms) such as salts of mono- or polynuclear aryl sulfonates having from about 0 to 16 carbon atoms in the alkyl group, e.g., sodium xylene sulfonate and sodium toluene sulfonate, sodium naphthalene sulfonate and the like. sodium dodecylbenzenesulfonate, magnesium tridecylbenzensulfonate and lithium or potassium pentapropylenebenezenesulfonate are available as the Bio-Soft® series, i.e, Bio-Soft® D-40 (Stephan Chemical Co., Northfield, Ill.). Useful naphthalene sulfonates include the alkali metal salts of alkyl naphthalene sulfonic acids (methyl naphthalene sodium sulfonate, Petro® AA, Petrochemicals Company, Inc., Forth Worth, Tex.).

Other useful classes of anionic surfactants include the alkali metal salts of sulfonsuccinic acid esters, e.g., dioctyl sodium sulfoxyccinate (Monawet® series, Mona Industries, Inc., Paterson, N.J.); sulfated higher fatty acid monoglycerides such as the sodium salt of the sulfated monoglyceride of coconut oil fatty acids and the potassium salt of the sulfated monoglyceride of tallow fatty acids; sodium $C_{14}$–$C_{16}$-alphaolefin sulfonates such as the Bio-Terge® series (Stephan Chemical Co.); alkali metal salts of higher fatty esters of low molecular weight alkyol sulfonic acids, e.g., fatty acid esters of the sodium salt of isethionic acids; the fatty ethanolamide sulfates; and the fatty acid amides of amino alkyl sulfonic acids, e.g., lauric acid amide of taurine.

Preferably, the combined amount of nonionic and anionic surfactants in the aqueous reactant phase will be about 0.5–15%, most preferably about 1.0–10%. The ratio of anionic surfactant:nonionic surfactant is preferably about 7.5–0.25:1, most preferably about 6–0.3:1.

Amphoteric detergents may also be incorporated into these hydrophilic foams. Preferred amphoteric surfactants are substantive to the hair and impart antistatic properties thereto. These detergents will be employed in a compatible proportion and manner with the nonionic-anionic surfactants, and may comprise about 0.25–5.0%, preferably 0.5–3.5% of the aqueous phase.

Preferred amphoteric surfactants for use in the present invention include those of the general formula: $RCONH(CH_2)_{2-3}N^+(CH_3)_2CH_2CO_2^-$ wherein R is a ($C_8$–$C_{22}$)alkyl group, e.g., cocamidoethyl betaine, cocamidopropyl betaine (Velvetex® BA-35 or BC-35, Henkel Corp.); lauramidopropyl betaine, myristamidopropyl betaine, stearamidopropyl betaine and the like.

Examples of other amphoteric detergents which may be employed include the fatty imidazolines, such as 2-coco-1-hydroxyethyl-1-carboxymethyl-1-hydroxylimidazoline and similar products made by reacting monocarboxylic fatty acids having chain lengths of 10-24 carbon atoms with 2-hydroxyethyl ethylenediamine and with monohalo monocarboxylic fatty acids having from 2 to 6 carbon atoms; the fatty beta-alanines such as dodecyl beta-alanine, the inner salt of 2-trimethylamino lauric acid, and betaines such as N-dodecyl-N,N-dimethylamino acidic acid and the like.

Particulate Absorbent

In some instances, it will be desirable to incorporate a particulate absorbent agent into the aqueous resultant phase employed to form the present foam pads. For example, about 1–20%, preferably about 2–15% of an absorbent mineral powder can help to dry sweaty hair and can help to impart a sheen to brushed hair via a polishing action. The mineral absorbent can also act as an internal reservoir for the organic solvent, enhancing its retention in the foam matrix prior to use.

Preferably, the absorbent mineral solids will be selected from one or more soft mineral solids (hardness 0.5-1 to 5-5.5). Soft mineral abrasives useful in the present invention include diatomaceous earth, wollastonite, gypsum, calcite, fluorite, cryolite, apatite, kaolinite clays, e.g., kaolin, kaolinite, anauxite, metakaolinite and the like.

Silane Coupling Agent

In the case of mineral absorbents such as silicates and aluminates which contain free Si-OH or Al-OH groups, it is preferable to covalently-bond the particulate minerals to the cured polymeric foam matrix via a minor amount of a silane coupling agent. The silane coupling agent functions to bond to both the polyurethane matrix and the surface of the particles of the mineral absorbent, thus chemically coupling the mineral particles into the polymeric matrix and preventing the particles from separating from the foam matrix during packaging or use. Silane-bound solid particles also clump less readily and so are more evenly dispersed throughout the matrix during foaming.

Useful silane-coupling agents may be selected from members of organosilicon monomers such as aminoalkyl(trisalkoxy)silanes which are characterized by the formula $R-SiX_3$, wherein R is an organofunctional group attached to silicon in a hydrolytically stable manner and X designates hydrolyzable groups which are converted to silanol groups upon hydrolysis. Most commonly, R comprises 3-aminopropyl or 3-ureidopropyl moiety which may be further separated from the silicon group by one or two $-NH(CH_2)_n-$ moieties wherein $n=1-2$. Preferably, X is an alkoxy group selected from the group consisting of methoxy, ethoxy, 2-methoxyethoxy or is acetoxy. Preferred silane-coupling agents are commercially available from Union Carbide as the A1100-A1160 series which includes 3-aminopropyltriethoxysilane, 3-aminopropyltrimethoxsilane (also available from Dow Corning as Z-6020), N-2-aminoethyle-3-amino-propyltrimethoxysilane, or 3-ureidopropyltriethloxysilane.

A slurry of the mineral particles is preferably prepared with about 50-70% by weight of the total water used to form the aqueous phase. The aqueous slurry is then treated with an amount of the silane-coupling agent equal to about 0.1-5% by weight of the amount of slurried solid. Completion of the hydrolysis reaction is assured by warming the slurry to at least about 21° C.-32° C., at which point the other components of the aqueous phase may be added, along with the remainder of the water. When the solid particles are coated in this fashion, the free amino groups of the coupling agent bind to the polymeric chains of the substrate during the foaming step, i.e., when the aqueous reactant phase and the polyurethane prepolymer resin are mixed together.

Inorganic Salt

It has been found desirable to add a small amount of an inorganic salt to the aqueous reactant phase to facilitate release of the interior aqueous phase from the foam. Such salts include alkaline metal and alkaline earth metal salts such as halides, sulfates, carbonates, bicarbonates, phosphates and the like, e.g., NaCl, KCl, LiCl, $CaCl_2$, NaI and the like.

Antimicrobial Agent

Minor but effective amounts of chemically compatible antimicrobial agents may also be included in the present aqueous phases to reduce or eliminate the bioburden of the foam pads during storage and following exposure to air.

Such agents include $C_1$-$C_5$-parabens (parahydroxy-($C_1$-$C_5$)alkylbenzoates), quaternary ammonium salts (benzalkonium chloride, benzethonium chloride, methylbenzethonium chloride cetalkonium chloride), 2-nitro-2-bromo-1,3-propanediol, cresol, chlorhexidine digluconate, hydantoin derivatives and the like.

The amount of any given antimicrobial agent or mixture thereof included will be dependent upon its potency and stability, but generally will not exceed about 1.0% by weight of the aqueous phase.

Fragrance

Minor but effective amounts of fragrance selected so as to be chemically compatible with the above-described ingredients are preferably included in the compositions of the present invention for cosmetic purposes. Useful fragrances will include, for instance, about 0.025-2%, preferably about 0.05-1.5%, of floral oils such as rose oil, lilac, jasmine, wisteria, apple blossom or compound bouquets such as spice, aldehydic, woody, oriental and the like.

Dermatological Agent

Minor but effective amounts of agents which can control skin conditions such as dandruff and psoriasis can also be incorporated into foam pads and pad-comb composites intended for human use. Therefore, up to about 2.5% of these agents can be incorporated in the aqueous phase. Useful dermatological agents include zinc pyrithione, chloroxine, acetylsalicylic acid, selenium sulfide, undecylenic acid and the like.

Insecticidal Agent

Minor but effective amounts of agents which can control or eliminate fleas, ticks and other pests when applied topically to the hair of an animal, such as a dog or cat, can also be incorporated into the present foam pads and pad-comb composites. Such agents include organophosphorous compounds and carbamates, as well as methoxychlor, rotenone and the pyrethrins. Useful organophosphorous insecticides include methyl parathion, diazinon, malathion and phorate. Useful carbamates include carbaryl, carbonfuran, propoxur, methomyl and aldicarb. Useful pyrethrins include allethrin, resmethrin, permethrin and fenvalerate. Due to the widely varying bioactivities of these compounds, the amount to be incorporated into the aqueous phase in order to achieve the release of an effective amount upon application of the pad or pad-comb combination to the coat of a given animal will necessarily vary, and will be determined by empirical experiments, as would be recognized by one of skill in the art of veterinary medicine.

Preferred Formulations

Therefore, a preferred aqueous reactant phase will comprise about 70-90%, preferably about 75-87.5% water; about 0.025-2.5%, preferably about 0.05-1.5% of polymeric organic conditioner; about 1-20%, preferably about 0.5-17.5%, most preferably about 5-15% of a water-immiscible organic solvent; about 0.1-5%, preferably about 0.25-4% of a nonionic surfactant; about 0.5-10%, preferably about 1-7.5% of an anionic surfactant; preferably in a weight ratio of about nonionic:anionic surfactant of about 1:0.25-7.5, preferably about 1:0.3-6; about 0.25-5%, preferably about 0.5-3.5% of amphoteric betaine detergent; and optionally about 0.1-2.5%, preferably about 0.5-2.25% of an inorganic salt. The aqueous reactant phase can also include about 1-20% particulate soft mineral absorbent and about 0.1-5% by weight of the absorbent of a silane-coupling agent. The slurry can further include minor but effective amounts of preservative, fragrance, antidandruff and/or insecticidal agent. The aqueous phase will not include any natural waxes or synthetic hydrocarbon waxes.

Preparation

The preparation of an aqueous reactant phase containing a particulate mineral absorbent and a silane-coupling agent is described above under Silane Coupling Agent. Generally, the entire amount of water is delivered into a suitable mixing vessel. Any cellulose-based polymeric conditioning agent is added at this point and dissolved with good agitation. The reaction mixture is then heated and the amphoteric surfactant, if any, is added, followed by the anionic surfactant and the nonionic surfactant. After dissolution of these ingredients has been achieved, the reaction mixture is cooled to 25° C. and stirred, while the inorganic salt and the synthetic polymeric or collagen-based conditioning agents are added. The preservative, antidandruff and/or insecticide is added at this point with continuous agitation. The solvent is slowly added and agitation continued in order to maintain a uniform dispersion until the foaming reaction is initiated.

A predetermined amount of the finished aqueous reactant phase is measured into an appropriately sized mixing vessel and stirred slowly at 25° C. To the aqueous phase is added a predetermined amount of prepolymer resin, which preferably has been heated to about 35° C.–45° C. Stirring is increased as the foaming reaction begins and the viscosity of the mixture increases. After about 10–20 sec., the foaming mixture is poured into appropriately sized molds which are covered as soon as full rise is achieved. Due to the steps taken to prevent moisture and solvent loss, the weight-percentages of ingredients in the interior aqueous phase is essentially similar to that present in the aqueous reactant phase.

After the bun is cured, it is sliced across the rise of the foam to yield the finished pads, which are enclosed in moisture and vapor-impermeable packages, such as those formed of metal foil, plastic films or paper-foil, paper-plastic composites. The applicators can be packaged individually or a plurality of sheets can be placed within a single container. Suitable packaging for premoisturized products is known in the art. For example, see U.S. Pat. Nos. 4,017,002; 3,057,467; and 4,219,129, the disclosures of which are incorporated by reference herein.

The Preferred and Alternate Embodiments Shown in the Drawings

The reference numeral 1, FIG. 1, generally designates a foam pad according to the present invention. The foam pad 1 may be constructed as previously indicated. Generally, the foam pad 1 includes agents therein, as previously described. The pad 1 is of a generally rectangular configuration. It will be understood, however, that a variety of shapes, sizes, and thicknesses can be readily accommodated in various arrangements and applications according to the present invention.

Figure 2:
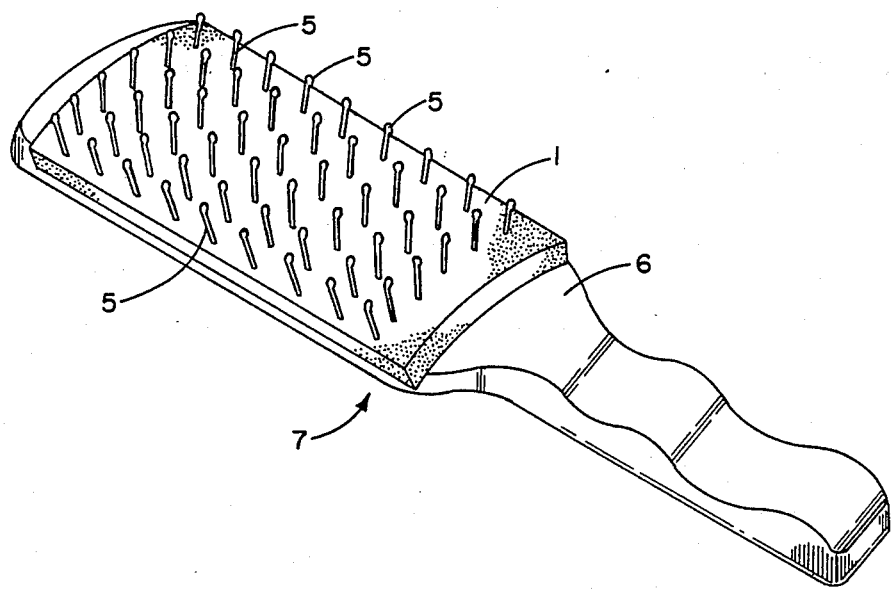
FIG. 2 is a perspective view showing a foam pad of FIG. 1, impaled upon a base or substrate, for use according to the principles of the present invention.

A preferred use of a foam pad, such as the pad 1 shown in FIG. 1, is illustrated in FIG. 2 of the drawings. Referring to FIG. 2, foam pad 1 is shown impaled upon tine means, in particular tines 5, of a substrate, in particular styling brush 6. The styling brush 6 may be of a conventional design having relatively rigid tines 5 thereon. The pad 1 is placed in a cooperative combination with the brush 6, simply by pressing a pad 1 over the tines 5. Generally, pads 1 made according to the present invention will be sufficiently porous for relatively easy mounting upon a conventional substrate such as brush 6.

It will be readily understood that a brush/pad combination 7 such as that shown in FIG. 2 can be effectively used for cleaning, conditioning or otherwise treating hair. As the tines 5 of the brush 6 are passed through the hair in a conventional manner, the hair is brought under contact with pad 1, for treatment as previously described. Generally, relatively rigid tines 5 are preferred, for ease of impaling of the pad 1 thereon, and also for effective brushing action in operational contact with the hair of a user. It is noted that the combination may be used to clean animal hair as well as human hair.

It will be readily understood that a variety of brush shapes and designs may be used. Thus, for example, the tines may be on a relatively planar surface, or a curved surface or even be positioned around the outside of a cylindrically shaped brush. Further, pads of shapes and sizes particularly developed for use in combination with the particular brush shape or size may be developed.

It will be further understood that brushes and pads, such as shown in FIG. 2, particularly adapted for use in combination with one another may be provided in a kit form. For example, a kit might include a single brush with a plurality of disposable pads for use in association therewith. Further, such a kit might include a plurality of different types of brushes, for different cleaning applications or use with different types of hair.

Figure 3:
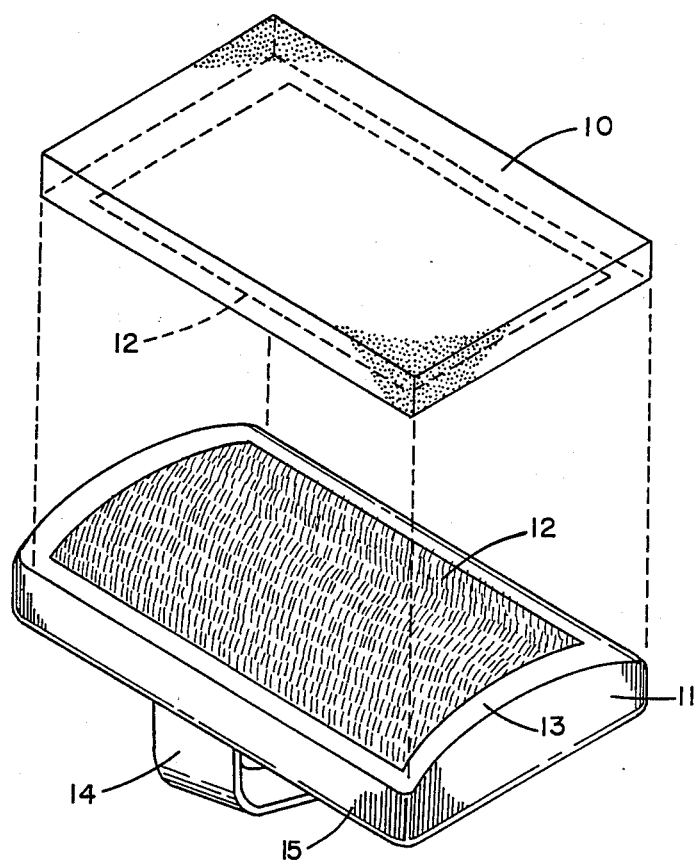
FIG. 3 comprises an exploded perspective view of a foam pad arrangement according to an alternate embodiment of the present invention.

An alternate embodiment according to the present invention is illustrated in FIG. 3. FIG. 3 generally represents an example in which a pad 10 is attached directly to a substrate or handle means, such as base 11 without tine means. Referring to FIG. 3, attachment is provided by means of a hook and loop connection system 12, such as that generally sold under the trade name Velcro ®. It will be understood that a variety of attachment systems may be used, including those involving use of an adhesive or the like. Generally, for uses according to the embodiment of FIG. 3, the pad 10 is attached to the base or substrate 11, again without tines. Thus, when desired, the pad 10 may be used for hair treatment, but not by actual brushing with tines. Preferably, the attachment system is such that a used, such as dirtied, pad 10 can be removed and replaced readily. The embodiment of FIG. 3 may be particularly useful for applications involving some, but relatively little, hair or when the skin is particularly sensitive to tines. For example, the arrangement might be preferred for cleaning the hair of the face, arms or legs.

Base 11 of FIG. 3 is a generally flat base having a slightly concave surface 13, on which the pad 10 is mounted. A handle 14, such as a strap or the like, is mounted on the backside 15 of the base 11. The strap may be easily grasped, as for example by placing a user's fingers thereunder. It will be understood that while the base 11 of FIG. 3 may be preferred for some applications, a variety of base designs may be utilized according to the principles of the present invention, including those resembling a conventional brush.

Figure 4:
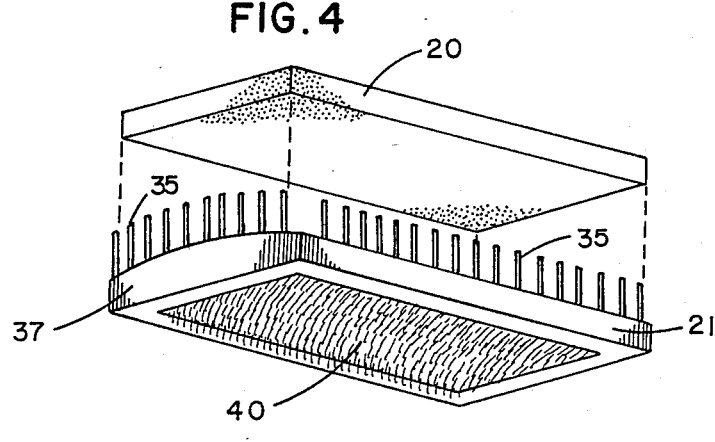
FIG. 4 comprises an exploded perspective view of a second alternate embodiment of a foam pad arrangement according to the present invention.

Referring to FIG. 4, a second alternate embodiment of the present invention is illustrated. FIG. 4 is an exploded view illustrating components of an alternate embodiment comprising a pad 20 and a removable and replaceable tine means 21. These may be attached to base means or substrate (not shown) as described below. A variety of handle designs may be used.

The pad 20 may be a pad according to the present invention, of any suitable size and shape for the particular brush arrangement involved. The pad 20 is utilized analogously to the pad 1 of FIG. 2. That is, pad 20 is impaled upon tines 35 of tine means 21, during use. Tine means 21, unlike the tines of FIG. 2, is readily separable from the base (not shown).

For the arrangement shown in FIG. 4, the tine means comprises a base portion 37 having tines 35 extending outwardly therefrom. The base portion 37 includes means for attachment to a front side of a base or substrate. For the embodiment shown in FIG. 4, a hook and loop connection system 40, such as that generally sold under the trade name Velcro ®, is employed. However, it will be understood that a variety of attachment mechanisms, preferably ones which facilitate rapid attachment and disconnection, may be used.

An advantage of an arrangement such as that shown in FIG. 4, is that the tine means 21 (and associated tines 35) can be easily removed and replaced, as desired. Thus tines of various lengths, population per given area, rigidity or the like, may be used. It is for seen that an arrangement such as FIG. 4 may be provided in a kit form, including at least one, disposable, pad 20, a variety of different, but analogously operating, members with tines 35, and at least one base or substrate, preferably with a handle thereon. It will be understood that a variety of shapes or designs of substrates 22 may be used, including ones having straps thereon providing an assembled arrangement analagous to that shown in FIG. 4, and also including ones (not shown) having handle arrangements providing an assembled arrangement analogous to that shown in FIG. 2.

From the figures previously described, it will be understood that a wide variety of arrangements utilizing foam pads according to the present invention may be provided. Generally, what is required is a convenient positioning of the foam pad such that it can be brought into contact with the surface or material to be treated. Brush arrangements such as that shown in FIG. 2 may be particularly convenient for use with human hair, or the hair of various animals such as domestic pets. The arrangement in FIG. 3 may be preferred for treating skin surfaces having some, but relatively little, hair thereon. The arrangement shown in FIG. 4 may be desired for maximum flexibility for treating hair of various lengths, coarseness, etc.

The invention will be further described by reference to the following detailed example.

Example I

Foam Pad-Brush Composites A. Protein-Containing Foam Sheet

A one-liter beaker equipped with mechanical stirring was charged with 552.6 g of distilled water and 0.70 g of a cationic cellulosic conditioner (Celquat ®, polyquaternium-4, National Starch and Chem. Corp., Bridgewater, N.J.) was sifted in with good agitation. Stirring was continued for 20 min. until a smooth, clear, particulate-free solution was obtained. The reaction mixture was heated to 35° C with continued stirring and 21.0 g of cocamidopropyl betaine (Velvetex ® BA-35, Henkel Corp.) was slowly added. Stirring was continued for 5 min. at 35° C. and then 49.0 g of TEA-lauryl sulfate (Standapol ® T, Henkel Corp.) was slowly added. After 5 min. of mixing at 35° C., 2.8 g of lauramide DEA (Standamid ® LD, Henkel Corp.) was added, and stirring continued for about 15 min., until the solid dissolved. Poloxamer 182 nonionic surfactant (Pluronic ® L-62, BASF-Wyandotte, 0.49 g) was added, and after 5 min. of mixing, 0.07 g of poloxomer 215 nonionic surfactant of Pluronic ® P-75, BASF-Wyandotte) was added, and mixing continued about 10 min. until dissolution was complete. The reaction mixture was allowed to cool to 25° C.

A 102.0 g portion of the resultant mixture was withdrawn and placed in a 250 ml beaker equipped with mechanical stirring. A solution of 1.20 g of hydrolyzed animal protein (Peptein ® 2000, 55% min. solids) was added. After 5 min. of stirring, 5.6 g of hydantoin preservative Dantogard, (Glyco, Greenwich, Conn.) was slowly added. After 5 min. of stirring, 9.60 g of isoparaffinic solvent (Isopar ® K, Exxon Corp.) was added, followed by 2.0 g of fragrance, with sufficient agitation to keep the solvent and fragrance uniformly dispersed throughout the aqueous phase.

A portion of 120 g of the resultant aqueous reactant phase was poured into a 500 ml beaker and maintained at 25° C. A 37° C. portion of 100 g of Hypol ® 3000 prepolymer resin was added and stirring continued for about 10 sec. as the foaming reaction started.

The foaming mixture (200 g) was poured into a rectangular high density polyethylene box (17.5 cm × 12.5 cm × 8.0 cm). The foam bun was covered after full rise was reached and allowed to cure for about 2–4 hours. The cured foam bun exhibited a density of 0.143 g/cc.

The cured bun was sliced with an electric slicer across the rise of the foam and then trimmed to a final dimension of 11.3 cm × 8.0 cm × 0.8 cm. The resilient, moist, open-celled foam pad was then packaged in a plastic-lined paper envelope to prevent loss of the volatile components.

The finished foam pad was easily impaled on the prongs of a hair styling brush, as depicted in FIG. 1. The resulting composite brush was effective when applied to dry hair to lift and absorb dirt, oil and perspiration. The composite brush imparted a conditioning effect on the hair and left a pleasant residual odor.

The formulation of this hydrophilic foam pad is summarized in Column A of Table I, below. The formulations listed as Examples IB-E were prepared as described for Example I, with the exceptions as noted.

TABLE I*

Hydrophilic Foam Pads
Formulation of Example I[a]

| Component | A | B | C | D | E | F |
|---|---|---|---|---|---|---|
| Water | 85.07 | 79.59 | 88.47 | 84.32 | 83.90 | 84.19 |
| Polmeric conditioner[b] | 0.10 | 0.10 | 0.10 | 1.95 | 1.50 | 2.17 |
| Cocoamidopropyl Betaine | 1.04 | 1.04 | 0.26 | 0.25 | 0.26 | 0.25 |
| TEA Lauryl Sulfate | 2.77 | 2.77 | 0.70 | 0.66 | 0.70 | 0.66 |
| Nonionic Surfactant[c] | 0.48 | 0.48 | 0.48 | 0.18 | 1.60 | 1.04 |
| Isopar ® K Solvent | 8.00 | 2.00 | 8.00 | 7.60 | 8.00 | 7.54 |
| Fragrance | 1.67 | 1.67 | 1.67 | 1.59 | 1.67 | 1.13 |
| Peptein ® 2000 Protein | 0.55 | — | — | — | 0.55 | 0.44[e] |
| NaCl | — | 2.03 | — | — | — | — |
| Ethanol[d] | — | — | — | 3.15 | 1.50 | 2.17 |
| Hydantoin[f] | 0.32 | 0.32 | 0.32 | 0.32 | 0.32 | 0.41 |

[a]Percent active component
[b]A-C: Celquat ® L-200; D: 0.1% Celquat ® L-200; 1.85 Gaffix ® VC-713; E: 1.50% PVP/VA E-635; F: 2.17% PVP/VA E-635.
[c]A-C: 0.4% Standamid ® LD, 0.07 Pluronic ® L-62; 0.01% Pluronic ® P-75; D: 0.10% Standamid ® LD, 0.07% Pluronic ® L-62; 0.01% Pluronic ® P-75; E: 0.10% Standamid ® LD; 1.50% Pluronic ® L-62; F: 0.09% Standamid ® LD; 0.95% Pluronic ® L-62.
[d]Contributed by Gaffix ® VC-713 or PVP/VA E-635.
[e]Lamepon ® PA-TR (TEA-Abietoyl Hydrolyzed Animal Protein).
[f]For A-E, Dantogard ®; F: DMDM Hydantoin.

Pads prepared from formulation IB released the aqueous phase more readily when impaled on a styling brush and brushed through the hair of a test subject. Hair cleaned and conditioned with pads prepared from formulation IC retained its buoyancy, e.g., was left fluffier, than hair treated with the other pads. This effect was apparently due to the lower total surfactant content.

The invention has been described with reference to various specific and preferred embodiments and techniques. However, it should be understood that many variations and modifications may be made while remaining within the spirit and scope of the invention.

What is claimed is:

1. A hair cleaning and conditioning pad comprising a , resilient, open-celled, hydrophilic polyurethane foam matrix, wherein bound to said matrix is an aqueous phase incorporating about 70-90% water, about 1-20% of a water-immiscible organic solvent, about 0.05-1.5% of a polymeric organic film-forming hair conditioner and about 0.5-15% of a mixture of an anionic surfactant and a nonionic surfactant.

2. The pad of claim 1 wherein the aqueous phase further comprises about 0.25-5% of an amphoteric betaine surfactant.

3. The pad of claim 1 wherein the ratio of anionic surfactant to nonionic surfactant is about 7.5-0.25:1.

4. The remover pad of claim 1 wherein the anionic surfactant comprises a sulfated fatty alcohol amine salt and the nonionic surfactant comprises a polyoxyalkylene block copolymer.

5. The pa of claim 1 wherein the aqueous phase further comprises about 0.5-2.5% of an inorganic alkali metal or alkaline earth metal salt.

6. The pad of claim 1 wherein the hair conditioner comprises a cationic organic polymer.

7. The pad of claim 6 wherein the hair conditioner comprises collagen or a collagen derivative.

8. The pad of claim 6 wherein the hair conditioner comprises a cationic cellulosic polymer.

9. The pad of claim 1 which further comprises a minor but effective amount of fragrance.

10. A hair cleaning and conditioning pad comprising a resilient, open-celled, hydrophilic polyurethane foam matrix, wherein bound in or on said matrix, is an aqueous phase incorporating about 75-87.5% water, about 0.025-7.5% of a polymeric organic film-forming, hair conditioner, about 5-15% of a water-immiscible organic solvent, about 0.1-5% of a nonionic surfactant, about 0.5-10% of an anionic surfactant, and an amount of an inorganic salt effective to substantially enhance the release of the aqueous phase from the foam matrix to the hair when the pad is pressed against the hair.

11. The pad of claim 10 wherein the water-immiscible organic solvent comprises an isoparaffin oil.

12. The pad of claim 10 wherein the aqueous phase further comprises about 1-20% of a particulate soft mineral absorbent which is silane-coupled to the foam matrix.

13. The pad of claim 10 wherein the aqueous phase further comprises minor but effective amounts of an antidandruff agent.

14. The pad of claim 10 wherein the aqueous phase further comprises a minor but effective amount of a topically active insecticide.

15. The pad of claim 10 wherein the aqueous phase further comprises a minor but efficient amount of fragrance.

16. The pad of claim 10 wherein the hair conditioner comprises hydrolyzed animal protein or a derivative thereof.

17. The pad of claim 10 wherein the hair conditioner comprises a cationic polymer.

18. The pad of claim 10 wherein the hair conditioner comprises a cationic cellulosic polymer.

19. An assembly for treatment of hair or the like; said assembly comprising:

(a) a base member;

(b) a hair cleaning pad member mounted on said base member; said pad member comprising a resilient, open-celled, hydrophilic polyurethane foam matrix, wherein bound to said matrix is an aqueous phase incorporating about 70-90% water, about 1-20% of a water-immiscible organic solvent, about 0.05-1.5% of a polymeric organic film-forming hair conditioner and about 0.5-1.5% of a mixture of an anionic surfactant and a nonionic surfactant.

20. An assembly according to claim 19 including tine means upon which said hair cleaning pad member is impaled.

21. An assembly according to claim 19 wherein:

(a) said base member comprises a brush having a plurality of tines projecting outwardly therefrom; and, (b) said pad member is impaled upon said plurality of tines.

22. A kit for providing cleaning and conditioning of hair; said kit including:

(a) at least one base member;

(b) at least one pad member mountable on said base member; said at least one pad member comprising a resilient, open-celled, hydrophilic polyurethane foam matrix, wherein bound to said matrix is an aqueous phase incorporating about 70-90% water, about 1-20% of a water-immiscible organic solvent, about 0.05-1.5% of a polymeric organic film-forming hair conditioner and about 0.5-1.5% of a mixture of an anionic surfactant and a nonionic surfactant.

23. A kit according to claim 22 wherein:

(a) said at least one member comprises a brush having a plurality of tines projecting outwardly therefrom; and, (b) said at least one pad member is operably impalable on said plurality of tines.

24. A method of cleaning and conditioning hair; said method comprising:

(a) providing an assembly comprising a base member with a pad member mounted hereon; said pad member comprising a resilient, open-celled, hydrophilic polyurethane foam matrix, wherein bound to said matrix is an aqueous phase incorporating about 70-90% water, about 1-20% of a water-immissible organic solvent, about 0.05-1.5% of a polymeric organic film-forming hair conditioner and about 0.5-1.5% of a mixture of an anionic surfactant and a nonionic surfactant; and, (b) manipulating said base member to bring said pad member into contact with hair to be cleaned and conditioned.

25. The method according to claim 24 including the steps of:

(a) providing tine means projecting through said pad member; and, (b) brushing said tine means through the hair to be cleaned and conditioned.

26. The method according to claim 24 wherein:

(a) said base member comprises a brush having a plurality of tines projecting outwardly therefrom; and (b) said pad member is impaled upon said plurality of tines.

* * * * *

UNITED STATES PATENT AND TRADEMARK OFFICE
CERTIFICATE OF CORRECTION

PATENT NO. : 4,856,541

DATED : August 15, 1989

INVENTOR(S) : George W. Kellett, et al.

It is certified that error appears in the above-identified patent and that said Letters Patent is hereby corrected as shown below:

At the Front page, Assignee, "Elizabeth" should read --Clifton--.

At Col. 4, line 21, "ensile" should read --tensile--.

At Col. 6, lines 34 and 35, "polymer" should read --poloxamer--.

At Col. 9, line 16, "3-aminopropyltrimethoxsilane" should read --3-aminopropyltrimethoxysilane--.

At Col. 15, line 21, "pa" should read --pad--.

Signed and Sealed this

Twenty-third Day of April, 1991

Attest:

HARRY F. MANBECK, JR.

*Attesting Officer*         *Commissioner of Patents and Trademarks*